(12) United States Patent
Mazur

(10) Patent No.: US 6,517,545 B1
(45) Date of Patent: Feb. 11, 2003

(54) SURGICAL CUTTING INSTRUMENT HAVING CONCAVE JAW TIPS

(76) Inventor: John B. Mazur, 513 N. First St., Geneva, IL (US) 60134-1432

( * ) Notice: Subject to any disclaimer, the term of this patent is extended or adjusted under 35 U.S.C. 154(b) by 0 days.

(21) Appl. No.: 09/695,356

(22) Filed: Oct. 24, 2000

(51) Int. Cl.⁷ .............................................. A61B 17/32
(52) U.S. Cl. ........................................ 606/83; 606/174
(58) Field of Search ...................... 606/1, 83, 205–210, 606/174, 167, 170, 175, 172, 184, 114, 79; 30/28, 178, 175, 26, 182; 600/562–565; 132/75.4, 75.5

(56) References Cited

U.S. PATENT DOCUMENTS

| | | | | |
|---|---|---|---|---|
| 450,703 | A | * 4/1891 | Price ............................. | 30/28 |
| 723,033 | A | * 3/1903 | Roux ............................ | 30/178 |
| 730,024 | A | 6/1903 | Kaufmann | |
| 810,402 | A | * 1/1906 | Friese ........................... | 30/28 |
| 1,021,999 | A | 4/1912 | Nicholls | |
| 1,363,164 | A | * 12/1920 | Oesterwitz ..................... | 30/28 |
| 1,841,847 | A | 1/1932 | Peters | |
| 2,566,626 | A | 9/1951 | Otto ............................. | 128/312 |
| 5,172,700 | A | 12/1992 | Bencini et al. ............... | 128/751 |
| 5,273,519 | A | 12/1993 | Koros et al. ................... | 606/83 |
| 5,368,596 | A | 11/1994 | Burkhart ...................... | 606/79 |
| 5,383,471 | A | 1/1995 | Funnell ....................... | 128/751 |
| 5,389,104 | A | 2/1995 | Hahnen et al. ............... | 606/174 |
| 5,395,375 | A | 3/1995 | Turkel et al. .................. | 606/83 |
| 5,537,747 | A | * 7/1996 | Cacciotti et al. ............... | 30/28 |
| 5,643,307 | A | 7/1997 | Turkel et al. ................. | 606/184 |
| 5,653,024 | A | * 8/1997 | Cartagenova ................... | 30/28 |
| 5,667,473 | A | 9/1997 | Finn et al. ..................... | 600/104 |
| 5,766,177 | A | 6/1998 | Lucas-Dean et al. ......... | 606/83 |
| 5,851,214 | A | 12/1998 | Larsen et al. ................. | 606/170 |
| 5,890,295 | A | 4/1999 | Wachtel et al. ............... | 30/191 |
| 5,922,002 | A | 7/1999 | Yoon ........................... | 606/170 |
| 5,964,777 | A | 10/1999 | Drucker ....................... | 606/180 |
| 5,983,498 | A | * 11/1999 | Lieberman et al. ............ | 30/28 |
| 6,009,880 | A | * 1/2000 | Weidlich ....................... | 30/28 |

FOREIGN PATENT DOCUMENTS

| | | | |
|---|---|---|---|
| DE | 30 23 671 A1 | 7/1982 | ........... A61B/10/00 |
| EP | 0 706 780 A2 | 4/1996 | ........... A61B/17/28 |
| EP | 0 835 637 A1 | 4/1998 | ........... A61B/10/00 |
| GB | 249289 | 3/1926 | |

OTHER PUBLICATIONS

Copy of International Search Report dated Jul. 4, 2001.

* cited by examiner

*Primary Examiner*—A. Vanatta
(74) *Attorney, Agent, or Firm*—Marshall, Gerstein & Borun

(57) ABSTRACT

A surgical instrument has a pair of opposed jaws constructed and arranged to open and close relative to one another. Each jaw has a proximal end connected to part of the surgical instrument, an opposite jaw tip end, and a confronting surface arranged facing the opposite jaw. A perimeter defines a boundary of the respective confronting surface and jaw tip end for each jaw. At least a first cutting edge portion is provided on a part of each jaw perimeter whereby that part defines the jaw tip end. Each first cutting edge portion is oriented extending toward the corresponding first cutting edge portion of the opposite jaw. Each first cutting edge portion is curved concavely inward toward the proximal end of the respective jaw.

18 Claims, 2 Drawing Sheets

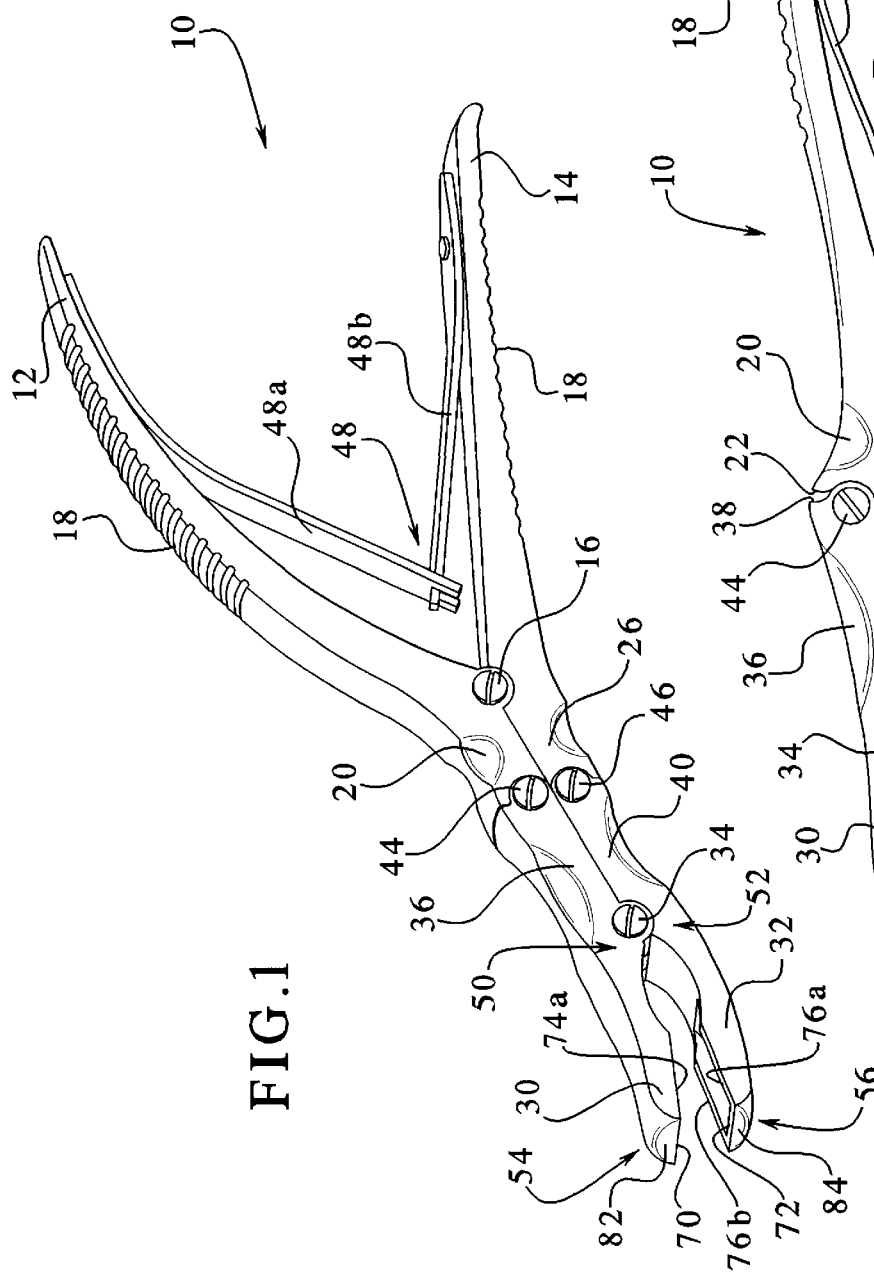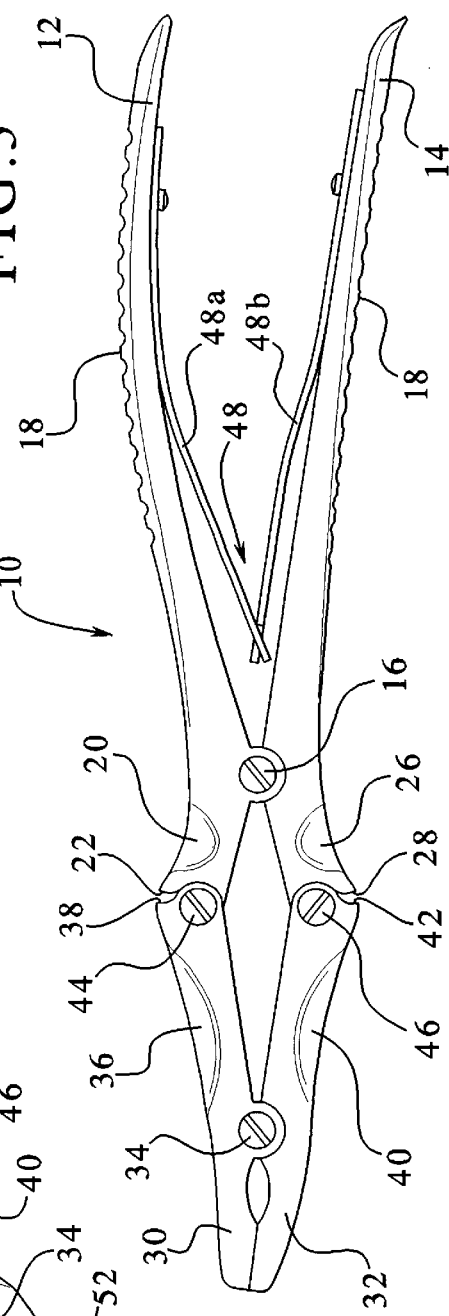

SURGICAL CUTTING INSTRUMENT HAVING CONCAVE JAW TIPS

FIELD OF THE INVENTION

The present invention relates generally to surgical instruments, and more particularly to a surgical instrument for cutting that has a pair of opposed cutting jaws with concavely curved jaw tips.

BACKGROUND OF THE INVENTION

There are many different types surgical instruments that include a pair of jaws and that are used to cut bone or other material during surgical procedures. One such instrument is known as a rongeur which has a pair of closeable jaws at one end that are utilized for cutting away bone, and particularly to smooth off a bone surface. A known rongeur instrument has a jaw tip end on each jaw that is outwardly curved or convex in a direction away from the tool or instrument. When a rongeur having a convex jaw tip end is utilized to smooth a bone surface, the device will typically leave small trenches or grooves in the bone surface because of the curvature of the jaw tip ends. The convex curve of the jaw tip leaves a small mirror-image concave groove or trench in the bone during each cut.

For many surgical procedures, this imprecise cutting technique leaves a satisfactory bone surface. However, for certain surgical procedures it is often desirable to leave a smooth bone surface or an outwardly or convex curved bone surface once material has been cut away. For example, when operating on the spine of an individual and approaching the anterior cervical spine, it is beneficial to be able to easily remove bone spurs or anterior osteophytes and also to leave the bone surface relatively smooth and slightly outwardly curved. Following such a procedure, a metal plate is sometimes screwed to the anterior surface of the vertebrae. The smooth and slightly outwardly curved anterior surface allows for better seating of the metal plate and screws. Utilizing a conventional convex curved jaw rongeur essentially prevents one from cutting away these osteophytes and simultaneously leaving the bone or vertebrae with a satisfactorily smooth and curved surface.

SUMMARY OF THE INVENTION

In order to overcome the above-described deficiencies in the prior art and other problems, a surgical instrument is provided in accordance with the teachings of the present invention. In one example, a surgical instrument has a pair of opposed jaws that are constructed and arranged to open and close relative to one another. Each jaw has a proximal end connected to part of the surgical instrument, an opposite end or free jaw tip end, and a confronting surface arranged facing the opposite jaw. A perimeter defines a boundary of the confronting surface and jaw tip end of each respective jaw. At least a first cutting edge portion is provided on a part of each jaw perimeter that defines the jaw tip end. Each first cutting edge is oriented such that it extends toward the corresponding first cutting edge portion of the opposite jaw. Each first cutting edge portion is curved concavely inward toward the proximal end of the respective jaw.

In one example, the surgical instrument can be a rongeur surgical instrument for cutting bone.

In one example, each jaw of the surgical instrument can have a pair of spaced apart second cutting edge portions provided on a substantial remaining part of each jaw perimeter. Each pair of second cutting edge portions can continue from opposite ends of the respective first cutting edge portion toward the proximal end of the jaw and can be oriented extending toward the corresponding pair of second cutting edge portions of the opposite jaw. In a further example, a concave hollow can be formed in the confronting surface surrounded by the respective perimeter of each jaw. The hollow can be arranged facing the hollow of the opposite jaw.

In one example, each jaw of the surgical instrument also can have a concave curved end face that is disposed at the jaw tip end and can have a surface curvature that corresponds to a curvature of the concavely curved first cutting edge portion of the respective jaw. In one example, the concavely curved first cutting edge portion of each jaw can have a curvature defined by a two-inch radius arc.

In one example constructed according to the teachings of the present invention, a rongeur surgical instrument has a pair of handles extending from a pivot that are moveable toward and away from one another. The rongeur instrument also includes a pair of opposed jaws that are positioned opposite the handles relative to the pivot and that are constructed and arranged to open and close relative to one another by movement of the handles. In one example, the rongeur surgical instrument is constructed wherein each jaw has a proximal end pivotally coupled to a portion of the instrument, an opposite free jaw tip end, and a confronting surface arranged facing the opposite jaw. Each jaw also has a perimeter that defines a boundary of the confronting surface and jaw tip end of each respective jaw. At least a first cutting edge portion is provided on a part of each jaw perimeter wherein that part of the perimeter defines the jaw tip end. Each first cutting edge portion is oriented extending toward the corresponding first cutting edge portion of the opposite jaw and each first cutting edge portion is curved concavely inward toward the proximal end.

In one example, the rongeur surgical instrument can also have a resilient spring disposed between the handles. The spring can be arranged to bias the handles away from one another and to bias the jaws toward the open position. In another example, the rongeur surgical instrument can be constructed from a stainless steel material.

In one example constructed according to the teachings of the present invention, a rongeur surgical instrument includes a pair of handles extending from a first pivot that are moveable toward and away from one another. Each handle has a drive arm that extends beyond the first pivot opposite the respective handle. A pair of opposed jaws extend from a second pivot and are constructed and arranged to open and close relative to one another. Each jaw has a proximal end with a lever arm extending beyond the second pivot opposite the respective jaw. Each lever arm is pivotally coupled to a corresponding one of the drive arms between the first and second pivots. Each jaw also has an opposite free jaw tip end and a confronting surface arranged facing the opposite jaw. A perimeter defines a boundary of the confronting surface and jaw tip end of each respective jaw. At least a first cutting edge portion is provided on a part of each jaw perimeter wherein that part of the perimeter defines the jaw tip end. Each first cutting edge portion is oriented extending toward the corresponding first cutting edge portion of the opposite jaw and is curved concavely inward toward the proximal end of the respective jaw.

Objects, features and advantages of the present invention will become apparent upon a review of the detailed description and accompanying drawing figures set forth herein.

There is a need for an improved surgical instrument that overcomes the deficiencies in the prior art described above. The detailed description and drawings herein provide one example of such an improved surgical instrument. Changes and modifications can be made to the disclosed examples and yet fall within the scope of the teachings of the present invention.

BRIEF DESCRIPTION OF THE DRAWINGS

FIG. 1 is a perspective view of one example of a surgical instrument constructed according to the teachings of the present invention showing the jaws of the instrument in an open position.

FIG. 3 is a side elevation view of the surgical instrument shown in FIG. 1 with the jaws in a closed position.

DETAILED DESCRIPTION OF THE PREFERRED EMBODIMENTS

Figure 2:
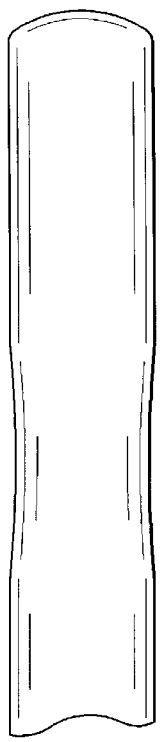
FIG. 2 is a bottom view of prior art jaws utilized on a surgical instrument such as that shown in FIG. 1.

One example of a surgical instrument constructed according to the teachings of the present invention is described herein. The invention is generally directed to a concave inwardly curved jaw tip end for a surgical instrument having a pair of jaws which open and close relative to one another in order to cut or shear a material such as bone. FIG. 1 generally illustrates a double action bone rongeur as the disclosed example. The jaw tip ends of the rongeur of FIG. 1 are shown as having a concave inward curve according to the present invention. FIG. 2 illustrates a prior art convex jaw tip end construction for such a surgical instrument. Though the exemplary instrument set forth herein is a double action bone rongeur, a single action rongeur, biopsy rongeur or other surgical instrument utilizing a pair of opposed jaw elements to cut or shear material can also utilize the teachings of the present invention.

Referring now to the drawings, FIG. 1 illustrates a surgical instrument in the form of a double action bone rongeur constructed according to the teachings of the invention. Orientation and arrangement terminology is utilized herein to simplify the description of the surgical instrument 10. Terms such as "upper", "lower", "front", "side", "distal", and "proximal" are utilized herein in order to describe relationships of certain components only. Use of these terms is not intended in any way to limit the construction of the described surgical instrument or the orientation of the instrument and components in any way.

With that in mind, the surgical instrument 10 includes an upper handle 12 and a lower handle 14 interconnected at one corresponding end by a first pivot 16. The handles 12 and 14 can pivot toward and away from one another about the first pivot 16 in order to operate the instrument. As an option, the exterior surface 18 of either of the handles 12 or 14 can include a surface treatment in order to improve the grip characteristics of the instrument. Knurling, bumps, grooves, high friction material, or the like can be added to either or both of the handles in order to accomplish an improved grip.

In the present example, a drive arm 20 extends from the upper handle 12 on the opposite side of the first pivot 16. The drive arm 20 terminates at a distal end 22. Similarly, a drive arm 26 extends from the lower handle on the opposite side of the first pivot and which terminates at a distal end 28. Movement of the handles 12 and 14 toward one another in this example moves the drive arm distal ends 22 and 28 away from one another. In an alternative example, the handles and drive arms can be configured similar to a pair of pliers, wherein the drive arms crisscross at the first pivot whereby movement of the handles toward one another moves the distal ends of the drive arms toward one another.

As illustrated in FIG. 1, the surgical instrument 10 also has a pair of jaws including an upper jaw 30 and a lower jaw 32 pivotally connected to one another at a second pivot 34 spaced from the first pivot 16. The upper and lower jaws 30 and 32 move about the second pivot 34 toward and away from one another.

In the present example, an upper lever arm 36 extends from the upper jaw 30 on the opposite side of the second pivot 34 and terminates at a proximal free end 38. Similarly, a lower lever arm 40 extends from the lower jaw 32 on the opposite side of the second pivot 34 and terminates at a proximal free end 42. Again, in this example, movement of the upper and lower jaws 30 and 32 toward one another moves the upper and lower lever arms 36 and 40 away from one another.

A pair of intermediate pivots, including an upper intermediate pivot 44 and a lower intermediate pivot 46, are provided to couple the jaws to the handles. The distal ends 22 and 28 of the drive arms 20 and 26 are coupled to the proximal ends 38 and 42 of the lever arms 36 and 40 at the intermediate pivots 44 and 46, respectively. This type of surgical instrument construction is known as a double action bone rongeur. Movement of the handles toward one another spreads the drive arms away from one another which also spreads the lever arms away from one another. This movement in turn draws the jaws to a closed position toward one another.

As discussed above, a pliers-type single action bone rongeur can also be utilized in conjunction with the teachings of the present invention. In such a construction, the handles 12 and 14 can be directly connected at a single pivot to the jaws 30 and 32. The upper handle can extend beyond the pivot and define a lower jaw and the lower handle can extend beyond the pivot and define an upper jaw, whereby the two components would crisscross. In the pliers configuration, movement of the handles toward one another moves the jaws toward one another as well. The double action construction as shown in FIG. 1 enables a manufacturer or designer to better manipulate the mechanical advantage characteristics of the surgical instrument.

The handles and jaws of the present invention can be provided or fabricated from any number of suitable materials. One preferable material is a high-quality stainless steel utilized for many surgical quality instruments. Surgical instruments typically require high precision, tight tolerance control during the manufacturing process and during use. However, the components of the invention are not to be limited to any particular material.

As an optional element, the surgical instrument 10 can also be provided with a resilient spring 48 or other suitable biasing element that is utilized to bias the handles away from one another. In the present example, one end of a spring section 48a is fixed to the upper handle 12 and one end of a spring section 48b is fixed to the lower handle 14. The free ends of spring sections 48a and 48b are coupled to one another between the handles. Movement of the handles toward one another flexes the resilient spring sections toward one another by overcoming the spring force of each section and closes the jaws. The resilient spring 48 returns the handles to an open jaw configuration when the handles are released. FIG. 1 illustrates the surgical instrument in the open jaw or at-rest position. FIG. 3 illustrates the surgical instrument 10 in the closed jaw configuration.

Figure 5:
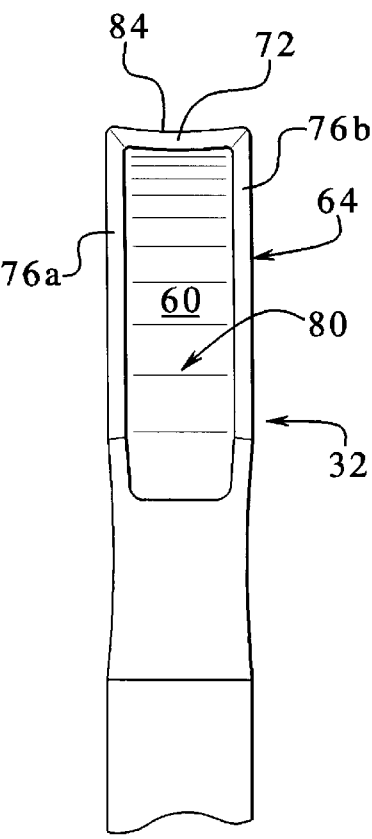
FIG. 5 is a top view of the lower jaw of the jaws shown in FIG. 4 wherein the upper jaw has been removed.

In the present example, the upper jaw 30 includes a proximal end 50 and the lower jaw 32 includes a proximal end 52 positioned nearer the second pivot 34. The opposite free end of each jaw defines an upper jaw tip end 54 and a lower jaw tip end 56, respectively. An upper confronting surface 58 (shown in FIG. 6) is provided on the upper jaw 30 and a lower confronting surface 60 (shown in FIG. 5) is provided on the lower jaw 32 arranged such that the upper and lower confronting surfaces 58 and 60 face one another.

An upper perimeter 62 of the upper jaw 30 defines a boundary of the upper confronting surface 58 and upper jaw tip end 54. Similarly, a lower perimeter 64 defines a boundary of the lower confronting surface 60 and lower jaw tip end 56 of the lower jaw 32. When the jaws are brought to the closed position as shown in FIG. 3, the confronting surfaces 58 and 60 and perimeters 62 and 64 move toward one another. A forward part of the upper perimeter 62 that defines the upper jaw tip end 54 is honed to provide an upper first cutting edge 70. Similarly, a forward part of the lower perimeter 64 that defines the lower jaw tip end 56 is honed to define a lower first cutting edge 72. When the jaws 30 and 32 are moved to the closed position, the upper and lower first cutting edges 70 and 72 contact one another or otherwise cooperate to provide a cutting or shearing action as determined by the particular surgical instrument characteristics.

A substantial remaining portion of the upper perimeter 62 on either side of forward part is also honed to provide a pair of upper second cutting edges 74a and 74b that continue from the upper first cutting edge 70. The second cutting edges are spaced apart on the sides of the upper jaw 30. The second cutting edge portions 74a and 74b flank the confronting surface 58 of the upper jaw. Similarly, a substantial remaining portion of the lower jaw perimeter 64 is honed or sharpened to define a pair of spaced apart lower second cutting edges 76a and 76b that flank the lower jaw confronting surface 60. The lower second cutting edges 76a and 76b continue from the lower first cutting edge 72 of the lower jaw.

Figure 6:
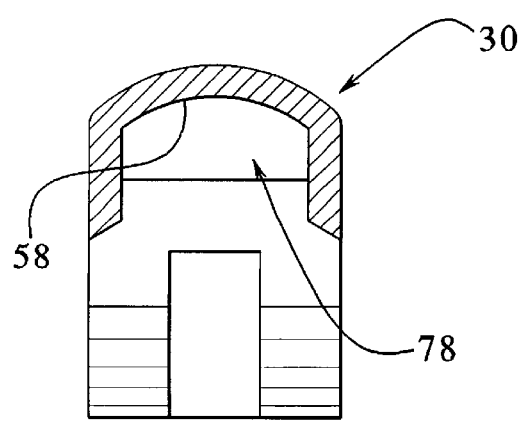
FIG. 6 is a lateral cross section taken along line VI—VI of the upper jaw shown in FIG. 4.

As is known in the art of these types of surgical instruments, one or both of the confronting upper and lower surfaces 58 and 60 can be hollowed, curved or recessed into the jaw to define a space between the two jaws when in the closed configuration of FIG. 3. In the present example, the upper jaw 30 has a hollow 78 and the lower jaw 32 has a hollow 80. The two hollow portions 78 and 80 of the jaws cooperate when the jaws are closed to define a cavity for holding material cut when utilizing the surgical instrument. As illustrated in FIG. 6 (upper jaw only), either one jaw or both jaws can include a significant depression or hollow to provide a substantial cavity between the closed jaws 30 and 32 for retaining a relatively large amount of cut-away material. When a surgical instrument such as the double action bone rongeur is utilized during surgery, it is preferable that when material is cut away, it remains captured in the instrument until removed from the body of the patient so that none of the material is lost within the wound or body cavity.

As discussed briefly above, FIG. 2 illustrates a prior art jaw tip end configuration for the upper and lower jaws 30 and 32 of such an instrument. The jaw tip ends are shown as being curved convexly or outward from the instrument.

Figure 4:
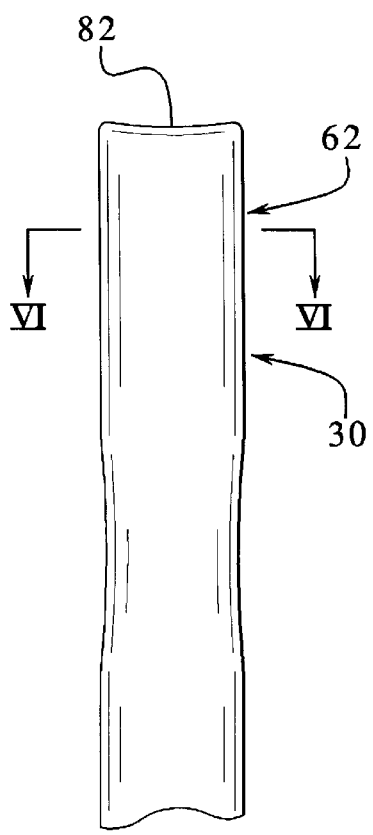
FIG.4 is a top view of the jaws of the surgical instrument shown in FIG. 3.

FIGS. 4 and 6 illustrate an improved and novel concave inwardly curved jaw tip end construction according to the teachings of the present invention. As shown in FIG. 4, both of the jaws 30 and 32 have a corresponding concave curvature. The jaw tip end and the first cutting edges 70 and 72 are concavely curved inward toward the proximal end of the respective jaws. In one example as illustrated in FIGS. 1 and 4, each jaw tip end has an end face 82 (upper jaw 30) and 84 (lower jaw 32). In this example, the end faces 82 and 84 are concavely curved inward in such a manner. The first cutting edges 70 and 72 of the upper and lower jaws, respectively, generally follow the same concave contour of the end faces 82 and 84 as illustrated.

In one example, the concave inward curvature of the jaw tip ends 54 and 56 and first cutting edges 70 and 72 of the surgical instrument are only slightly curved. As an example, the tip ends can have a curvature defining an arc for a two-inch radius. As will be evident to those of ordinary skill in the art, the particular width of the jaw tip ends 54 and 56 and the particular curvature of the first cutting edges 70 and 72 can vary according to the needs of a particular surgical instrument. As shown in FIG. 6, a plane "A" of the cutting edges 70 and 72 and the cutting edges 74a, 74b and 76a, 76b remains consistent.

The inward or concave curvature of the jaw tip ends of the surgical instrument described herein permits material such as bone spurs or bone material to be removed while simultaneously leaving a relatively smooth surface on the bone.

For example, during certain types of back surgery, bone spurs or osteophytes are cut away from vertebrae. Utilizing a surgical instrument according to the prior art of FIG. 2, the convex curvature of the jaw tip end leaves tiny grooves in the bone that mirror the curvature of the jaw tip end. In contrast, the surgical instrument of the present invention will leave no such groove or indents in the cut away bone and will instead leave a relatively smooth and slightly outwardly curved bone surface.

Although certain surgical instruments constructed in accordance with the teachings of the present invention have been described herein, the scope of coverage of this patent is not limited thereto. On the contrary, this patent covers all embodiments of the teachings of the invention that fairly fall within the scope of the appended claims, either literally or under the doctrine of equivalents.

What is claimed is:

1. A surgical instrument comprising:
   a pair of opposed jaws constructed and arranged to open and close relative to one another, each jaw having a proximal end connected to part of the surgical instrument, an opposite free jaw tip end, a confronting surface arranged facing the opposite jaw, and a respective longitudinal axis;
   a perimeter that defines a boundary of the confronting surface and jaw tip end of each respective jaw;
   a concave hollow in the confronting surface surrounded by the respective perimeter, the hollow arranged facing the hollow of the opposite jaw; and
   at least a first cutting edge portion provided on a part of each jaw perimeter that defines the jaw tip end, wherein each first cutting edge portion is arranged extending toward the corresponding first cutting edge portion of the opposite jaw, is curved concavely inward toward the proximal end of the respective jaw, and has a bisecting line that bisects an arc of the first cutting edge portions and is oriented generally parallel to the longitudinal axis of the respective jaw, and wherein the angle of the bisecting line of the arc is fixed relative to the longitudinal axis of the respective jaw.

2. A surgical instrument according to claim 1, wherein the surgical instrument is a rongeur instrument.

3. A surgical instrument according to claim 1, wherein each jaw further comprises:
a pair of spaced apart second cutting edge portions provided on a substantial remaining part of each jaw perimeter, each pair of second cutting edge portions extending from the respective first cutting edge portion toward the proximal end of the jaw and oriented extending toward the corresponding pair of second cutting edge portions of the opposite jaw.

4. A surgical instrument according to claim 1, wherein each jaw further comprises:
a concave curved end face disposed at the jaw tip end having a surface curvature that corresponds to a curvature of the concavely curved first cutting edge portion of the respective jaw.

5. A surgical instrument according to claim 1, wherein the concavely curved first cutting edge portions each have a curvature defined by a 2 inch radius arc.

6. A surgical instrument according to claim 1, wherein the surgical instrument further comprises:
a pair of handles pivotally connected at one end to facilitate opening and closing of the jaws.

7. A surgical instrument according to claim 1, wherein the surgical instrument further comprises:
a resilient biasing element disposed between the handles and arranged to bias the handles away from one another and to bias the jaws toward the open position.

8. A rongeur surgical instrument comprising:
a pair of handles extending from a pivot and being movable toward and away from one another;
a pair of opposed jaws positioned opposite the handles relative to the pivot and being constructed and arranged to open and close relative to one another by movement of the handles, each jaw having a proximal end pivotally coupled to a portion of the instrument, an opposite free jaw tip end, a confronting surface arranged facing the opposite jaw, and a respective longitudinal axis;
a perimeter that defines a boundary of the confronting surface and jaw tip end of each respective jaw;
a concave hollow in the confronting surface surrounded by the respective perimeter, the hollow arranged facing the hollow of the opposite jaw; and
at least a first cutting edge portion provided on a part of each jaw perimeter that defines the jaw tip end, wherein each first cutting edge portion is arranged extending toward the corresponding first cutting edge portion of the opposite jaw, is curved concavely inward toward the proximal end of the respective jaw, and has a bisecting line that bisects an arc of the first cutting edge portions and is oriented generally parallel to the longitudinal axis of the respective jaw, and wherein the angle of the bisecting line of the arc is fixed relative to the longitudinal axis of the respective jaw.

9. A rongeur surgical instrument according to claim 8, further comprising:
a resilient biasing element disposed between the handles and arranged to bias the handles away from one another and to bias the jaws toward the open position.

10. A rongeur surgical instrument according to claim 8, wherein each jaw further comprises:
a pair of spaced apart second cutting edge portions provided on a substantial remaining part of each jaw perimeter, each pair of second cutting edge portions extending from the respective first cutting edge portion toward the proximal end of the jaw and oriented extending toward the corresponding pair of second cutting edge portions of the opposite jaw.

11. A rongeur surgical instrument according to claim 8, wherein each jaw further comprises:
a concave curved end face disposed at the jaw tip end having a surface curvature that corresponds to a curvature of the concavely curved first cutting edge portion of the respective jaw.

12. A rongeur surgical instrument according to claim 8, wherein the concavely curved first cutting edge portions each have a curvature defined by a 2 inch radius arc.

13. A rongeur surgical instrument according to claim 8, wherein the handles and jaws are fabricated from a stainless steel material.

14. A rongeur surgical instrument comprising:
a pair of handles extending from a first pivot and being movable toward and away from one another, each handle having a drive arm extending beyond the first pivot opposite the respective handle;
a pair of opposed jaws extending from a second pivot and constructed and arranged to open and close relative to one another, each jaw having a lever arm extending beyond the second pivot opposite the corresponding jaw and being pivotally coupled to a corresponding one of the drive arms between the first and second pivots, each jaw also having an opposite free jaw tip end, a confronting surface arranged facing the opposite jaw; and a respective longitudinal axis;
a perimeter that defines a boundary of the confronting surface and jaw tip end of each respective jaw;
a concave hollow in the confronting surface surrounded by the respective perimeter, the hollow arranged facing the hollow of the opposite jaw; and
at least a first cutting edge portion provided on a part of each jaw perimeter that defines the jaw tip end, wherein each first cutting edge portion is arranged extending toward the corresponding first cutting edge portion of the opposite jaw, is curved concavely toward the proximal end of the respective jaw, and has a bisecting line that bisects an arc of the first cutting edge portions and is oriented generally parallel to the longitudinal axis of the respective jaw.

15. A rongeur surgical instrument according to claim 14, further comprising:
a resilient biasing element disposed between the handles and arranged to bias the handles away from one another and to bias the jaws toward the open position.

16. A rongeur surgical instrument according to claim 14, wherein each jaw further comprises:
a pair of spaced apart second cutting edge portions provided on a substantial remaining part of each jaw perimeter, each pair of second cutting edge portions extending from the respective first cutting edge portion toward the proximal end of the jaw and oriented extending toward the corresponding pair of second cutting edge portions of the opposite jaw.

17. A rongeur surgical instrument according to claim 14, wherein each jaw further comprises:
a concave curved end face disposed at the jaw tip end having a surface curvature that corresponds to a curvature of the concavely curved first cutting edge portion of the respective jaw.

18. A rongeur surgical instrument according to claim 16, wherein the concavely curved first cutting edge portions each have a curvature defined by a 2 inch radius arc.

* * * * *